United States Patent
Rasmusson et al.

(10) Patent No.: US 10,294,470 B2
(45) Date of Patent: May 21, 2019

(54) ELECTRONIC EXPRESSION OF THE INWARD RECTIFIER IN CARDIOCYTES DERIVED FROM HUMAN INDUCED PLURIPOTENT STEM CELLS

(71) Applicant: The Research Foundation for The State University of New York, Amherst, NY (US)

(72) Inventors: Randall Lee Rasmusson, Pendleton, NY (US); Glenna C. L. Bett, Albion, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 405 days.

(21) Appl. No.: 14/891,069

(22) PCT Filed: May 19, 2014

(86) PCT No.: PCT/US2014/038611
§ 371 (c)(1),
(2) Date: Nov. 13, 2015

(87) PCT Pub. No.: WO2014/186793
PCT Pub. Date: Nov. 20, 2014

(65) Prior Publication Data
US 2016/0083715 A1 Mar. 24, 2016

Related U.S. Application Data

(60) Provisional application No. 61/824,507, filed on May 17, 2013.

(51) Int. Cl.
*C12N 13/00* (2006.01)
*G01N 27/00* (2006.01)
*G01N 33/50* (2006.01)
*G01N 33/487* (2006.01)

(52) U.S. Cl.
CPC ............. *C12N 13/00* (2013.01); *G01N 27/00* (2013.01); *G01N 33/48728* (2013.01); *G01N 33/5073* (2013.01)

(58) Field of Classification Search
CPC ............. G01N 33/48728; G01N 27/00; G01N 33/5073; C12N 13/00
See application file for complete search history.

(56) References Cited

U.S. PATENT DOCUMENTS 6,700,427 B1 3/2004 Sherman
2010/0189701 A1 7/2010 Cohen et al.

OTHER PUBLICATIONS

Ma, J., et al., High purity human-induced pluripotent stem cell-derived cardiomyocytes: electrophysiological properties of action potentials and ionic currents, American Journal of Physiology Heart and Circulatory Physiology, American Physiological Society, Sep. 2, 2011, vol. 301, No. 5, 11 pages.

(Continued)

*Primary Examiner* — Gautam Prakash
(74) *Attorney, Agent, or Firm* — Hodgson Russ LLP (57) ABSTRACT

Systems and methods are provided for improving action potential morphology in iPSC-derived cardiac myocytes and utilizing such myocytes. Improved morphology may include, for example, physiological resting membrane potentials. Membrane voltages of the myocyte are measured and a synthetic inward rectifying current is applied to the myocyte based on the membrane voltage.

7 Claims, 7 Drawing Sheets

(56) References Cited

OTHER PUBLICATIONS

Davis et al., Cardiomyocytes derived from pluripotent stem cells recapitulate electrophysiological characteristics of an overlap syndrome of cardiac sodium channel disease, Circulation, vol. 125, No. 25, pp. 3079-3091. Jun. 26, 2012.
Knollmann et al., Induced Pluripotent Stem Cell-Derived Cardiomyocytes: Boutique Science or Valuable Arrhythmia Model?, Circulation Research, vol. 112, No. 6, pp. 969-976. Mar. 15, 2013.
Berecki et al., Cardiac channelopathies studied with the dynamic action potential-clamp technique, Methods Mol Biol. 2007;403:233-50. Jan. 1, 2007.
Liu, Specifically Enhancing Inward Rectified Potassium Current (Ik1): a New Antiarrhythmic Pathway, Chinese Doctoral Dissertations Full-Text Database Medicine and Health Sciences, No. 9 Aug. 16, 2016.
Shang et al., Kinetics reconstruction of cardiac delay rectifier K+ current, Chinese Heart Journal, vol. 12, No. 4, pp. 255-256. Dec. 31, 2000.
Shang et al, Computer Reconstruction of Kinetic Model of Myrocardial Inward Rectifier K+ current IK1, The Journal of the Fourth Military University, vol. 22, No. 20, pp. 1885. Dec. 31, 2001.

Fig. 8

ELECTRONIC EXPRESSION OF THE INWARD RECTIFIER IN CARDIOCYTES DERIVED FROM HUMAN INDUCED PLURIPOTENT STEM CELLS

CROSS REFERENCE TO RELATED APPLICATIONS

This application claims priority to U.S. Provisional application No. 61/824,507, filed on May 17, 2013, the disclosure of which is incorporated herein by reference.

STATEMENT REGARDING FEDERAL FUNDING

This invention was made with government support under grant numbers HL093631 and HL062465 from the National Institutes of Health. The government has certain rights in the invention.

BACKGROUND OF THE INVENTION

The term "Induced pluripotent stem cells," or iPSCs, refers to a type of pluripotent stem cell artificially prepared from a non-pluripotent cell. Cardiac myocytes derived from iPSCs are a useful experimental system which has great potential. They offer an innovative human preparation for cardiac repair, drug safety design and testing, clinical diagnosis, and research. Cardiac myocytes derived from iPSCs offer the opportunity to work on cells which recapitulate the activity of healthy human cardiac myocytes, which are otherwise rarely available for comprehensive experimental investigation. Human iPSC-derived cardiac myocytes offer the ability to develop predictive tools for cardiac function.

Despite the possibilities of cardiac myocytes derived from iPSCs, problems with this approach have been noted, leading to serious concerns about their use in studying arrhythmogenic mechanisms and drug safety screening. Action potentials (APs) from human cardiac myocytes derived from iPSCs are often referred to as an "immature phenotype." The lack of the expected classic spike and dome type of AP morphology has led to serious concerns over the ability of human cardiac myocytes derived from iPSCs to be used to study the genetic basis of Brugada syndrome and other J-wave or early repolarization related arrhythmias. In addition to an apparently less complicated repolarization profile, iPSC cardiac myocytes also show spontaneous contractile activity. This contractile activity is accompanied by corresponding diastolic depolarization resulting in spontaneous APs. Thus, while iPSCs can be induced to develop into cardiac myocyte-like cells, they are not able to display electrophysiological properties that would allow use of these cells in evaluation of cardiac cell function or use for screening of drugs affecting cardiac cells.

SUMMARY OF THE INVENTION

In the present disclosure, we evaluate the role of reduced inward rectifying current ($I_{K1}$) in human iPSC-derived myocytes by electronically adding an $I_{K1}$ component to these cardiac myocytes under current clamp. This approach indicates the strong influence of $I_{K1}$ and the degree to which its expression produces major physiological differences in repolarization and potentially arrhythmogenic behavior. We demonstrate that artificial replacement of $I_{K1}$ produces human iPSC-derived cardiac myocytes with APs which much more closely resemble the behavior of APs from freshly isolated human cardiac myocytes.

In one aspect, this disclosure provides a system to improve action potential morphology in iPSC-derived cardiac myocytes. Improved AP morphology may include, for example, physiological resting membrane potentials, and spike and dome action potentials. The system comprises a patch clamp having an electrode for measuring a membrane voltage of the myocyte and a generating circuit in electrical communication with the electrode. The generating circuit is configured to calculate a value of an inward rectifying current based on the membrane voltage and apply a synthetic inward rectifying current to the myocyte based on the calculated value.

This method has many applications, and will enable comprehensive analysis of this electrophysiological system and also allow screening of drugs specific for atrial or for ventricular cell defects. iPSC cardiac myocytes of the present disclosure can be used in the interpretation of channelopathies, drug screening, and the assessment of potential arrhythmogenesis. By eliminating many of the non-physiological consequences of spontaneous activity and unstable behavior, this tool will be useful for studying the dynamics of repolarization. It has applications for research studies looking at genetic regulation of repolarization in disease states, as well as serving as an aid in the interpretation of data from drug studies and the proarrhythmic potential of safety screens. It could also be used to modify treatment regimes based on the data obtained.

In one aspect, this disclosure provides a method for producing action potentials having improved morphology in iPSC-derived cardiac myocytes. The method comprises the steps of measuring a membrane voltage of a myocyte; calculating a value of an inward rectifying current based on the measured membrane voltage; and applying a synthetic inward rectifying current to the myocyte thereby causing the myocyte to produce action potentials having improved morphology.

In one aspect, this disclosure provides a method for distinguishing iPSC-derived cardiac myocytes having atrial cell-like electrical features from iPSC-derived cardiac myocytes displaying ventricular cell-like electrical features.

In one aspect, this disclosure provides a method for screening candidate agents that can affect the electrical characteristics of atrial cells or ventricular cells. The method comprises identifying whether an iPSC-derived cardiac myocyte is displaying an atrial or a ventricular phenotype and then testing the effect of putative drugs that affect atrial or ventricular function.

iPSC cardiac myocytes will be able to be used in the interpretation of channelopathies, drug screening, and the assessment of potential arrhythmogenesis. By eliminating many of the non-physiological consequences of spontaneous activity and unstable behavior, this tool will be useful for studying the dynamics of repolarization. It has applications for research studies looking at genetic regulation of repolarization in disease states, as well as serving as an aid in the interpretation of data from drug studies and the proarrhythmic potential of safety screens. It could also be used to modify treatment regimes based on the data obtained.

BRIEF DESCRIPTION OF THE FIGURES

FIG. 4: APs before and after synthetic $I_{K1}$ expression and pacing. (A) Spontaneous ventricular-type cells. These cells show a rounded AP, but are difficult to distinguish because the relatively high diastolic potential reduces $dV/dt_{max}$. The "shoulder" of the AP is blurred by slow phase IV repolarization. (B) Electronic expression of $I_{K1}$ in (A) restores a normal resting potential which removes $I_{Na}$ inactivation, thereby increasing $dV/dt_{max}$ and resetting other currents. The resetting of currents such as $I_{to}$ produces the classical "spike and dome" morphology of ventricular cells. (C) Spontaneously beating atrial-like cells, which have a morphology which is difficult to distinguish from ventricular or nodal cells. (D) Electronic expression of $I_{K1}$ reveals the atrial nature of the cells in panel c. As with ventricular cells, the negative resting potential restores a normal dV/dt and reveals the characteristic spike and low more triangular repolarization phase typical of atrial cells. (E,F) Details of repolarization of (E) atrial-like and (F) ventricular-like APs on expanded time scale. (G) Scatterplot of the ratio $APD_{30}/APD_{90}$ vs. $APD_{30}$ for cells with electronic expression of $I_{K1}$.

FIG. 5. Effects of calcium channel agonist BayK8644. (A) APs stimulated at a cycle length of 4 s. Intrinsic automaticity caused some APs to be very shortened, and some stimuli occurred during repolarization from a preceding spontaneous beat. Three traces are overlaid. (B) Same cell, with 1 μM BayK8644. BayK8644 caused calcium loading which terminated spontaneous activity. Stimulated APs showed abnormal behavior with severely shortened repolarization and little evidence of regenerative depolarization. Three traces are overlaid. (C) Same cell as (A,B) but with electronic expression of $I_{K1,synthetic}$. The AP has normal spike and dome morphology, and consistent $APD_{90}$. These traces were recorded prior to B. (D) Same cell as in (A, B, C), with $I_{K1,synthetic}$ and 1 μM of BayK8644. APD is prolonged, and the arrhythmogenic phenomenon of alternans is observed. Some APs were interrupted by the subsequent stimulus. Despite the time invariant nature of $I_{K1}$, electronic expression of $I_{K1}$ makes the observation of the dynamic phenomenon of alternans readily observable. In addition to QT prolongation, changes in the threshold for alternans are an important cellular index of pro-arrhythmic potential. (E) $APD_{90}$ is little changed by $I_{K1,synthetic}$ (n=7). This may seem paradoxical, but the net effect of the addition of $I_{K1}$ is prolongation of the dome part of repolarization and increasing the rate of the final stages (or foot) of repolarization. The result is only a modest change in $APD_{90}$. (F) Ratio of $APD_{90}$ with/without BayK8644 shows a major increase in APD with $I_{K1,synthetic}$ expression and an anomalous decrease in $APD_{90}$ without it.

DETAILED DESCRIPTION OF THE INVENTION

The present disclosure provides a method of imparting physiological action potential morphology, relative to native cells, to iPSC-derived cardiac myocytes. The method comprises electronically adding an $I_{K1}$ component to cardiac myocytes under current clamp. We demonstrate that artificial replacement of $I_{K1}$ produces human iPSC-derived cardiac myocytes with APs which much more closely resemble the behavior of APs from freshly isolated human cardiac myocytes.

The iPSCs can be prepared from a non-pluripotent cell, typically an adult somatic cell, or terminally differentiated cell, such as fibroblast, a hematopoietic cell, a myocyte, a neuron, an epidermal cell, or the like, by introducing into the cells or contacting the cells with reprogramming factors. Induced pluripotent stem cells can be differentiated into cardiac myocytes. For example, adult human fibroblasts can be transfected with transcription factors Oct4, Sox2, c-Myc and/or Klf4 using retroviral transduction, or with Oct4, Sox2, Nanog and Lin28 using lentivirus transduction. For a discussion of iPSCs derived cardiac myocytes, see U.S. Pat. No. 8,415,155, the disclosure of which is incorporated herein by reference.

After reprograming factors are introduced into somatic cells, these cells may be cultured in a medium sufficient to maintain the pluripotency and the undifferentiated state. Culturing methods and media for the maintaining the iPSCs in culture are well-known.

Cardiomyocyte lineage cells can be obtained from undifferentiated stem cells by culturing or differentiating in a special growth environment that enriches for cells with the desired phenotype. For example, this can be achieved by outgrowth of the desired cells, or by inhibition or killing of other cell types. Details can be found in U.S. Pat. No. 8,415,155. This provides iPSC-derived cardiac myocytes. Additionally, IPSC-derived cardiac myocytes are also commercially available.

To record electrical activity from the iPSCs derived cardiac myocytes, whole cell voltage or current clamp techniques can be used. Generally, these techniques involve formation of a gigaseal using conventional methods.

The iPSC-derived cardiac myocytes typically generate action potentials having a "rounded" morphology with a sluggish upstroke. The high MDP reduces the dV/dtmax and it is difficult to distinguish ventricular from atrial cells based on the AP morphology.

Figure 1:
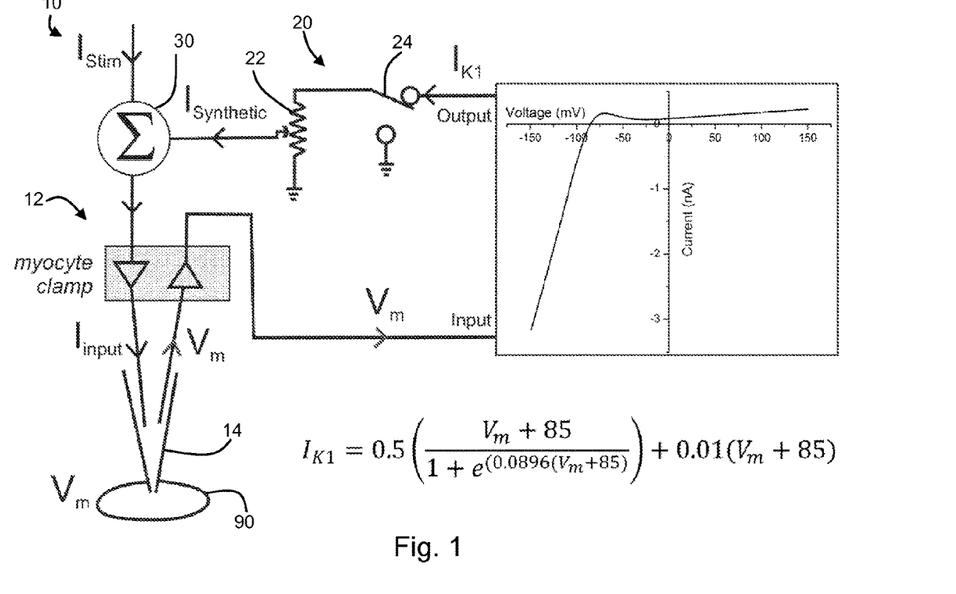
FIG. 1: Organization of the electronic $I_{K1}$ current expression system. $I_{K1,Synthetic}$ is generated in real time in response to the myocyte membrane potential. For all cells in this study the potentiometer was set to provide a standard outward current of 150 pA at −75 mV.

With reference to FIG. 1, the present disclosure may be embodied as a system 10 for improving action potential morphology in an iPSC-derived cardiac myocyte 90. Improved action potential morphology includes, for example, a stable physiological resting membrane potential and/or physiological action potential morphology. The system 10 comprises a patch clamp 12 as is known in the art. The patch clamp 12 is a single-electrode apparatus configured for whole-cell measurement. As such, the patch clamp 12 comprises an electrode 14. The electrode 14 may be, for example, a glass micropipette filled with a conductive solution. Such an exemplary electrode may be configured to form a gigaohm seal with the cell to be measured. The patch clamp 12 is configured to measure a membrane voltage ($V_m$) of the myocyte 90.

The patch clamp 12 is configured to measure the action potential of the myocyte 90. In some embodiments, the patch clamp 12 is configured as a current clamp and provides a stimulation current ($I_{STIM}$) to the cell 90 by way of the electrode 14. As such the patch clamp 12 may be configured to record the action potential of the cell 90 over time by sampling (measuring) the membrane voltage at a sampling frequency.

The system 10 comprises a generating circuit 20 in electrical communication with the electrode 14 of the patch clamp 12. The generating circuit 20 is configured to receive an electrical signal from the electrode 14, where the electrical signal indicates a measured membrane voltage. In this way, the generating circuit 20 receives a measured membrane voltage from the electrode 14. The generating circuit 20 is configured to calculate a value of an inward rectifying current ($I_{K1}$) based on a membrane voltage from the electrode 14. For example, the inward rectifying current may be calculated from the membrane voltage according to the equation:

$$I_{K1} = 0.5\left(\frac{V_m + 85}{1 + e^{0.0896(V_m+85)}}\right) + 0.01(V_m + 85). \quad (1)$$

Other relationships between membrane voltage and inward rectifying current will be apparent in light of the present disclosure and should be included in the scope of some embodiments.

The generating circuit 20 is further configured to provide a synthetic inward rectifying current ($I_{SYNTHETIC}$) to the electrode 14. The synthetic inward rectifying current provided by the generating circuit 20 corresponds to the value of $I_{K1}$ calculated by the generating circuit 20. In some embodiments the synthetic inward rectifying current is equal to the calculated value of the inward rectifying current ($I_{SYNTHETIC}=I_{K1}$). In some embodiments $I_{SYNTHETIC}$ may be different from $I_{K1}$. For example, the generating circuit 20 may further comprise a potentiometer 22, and the provided current ($I_{SYNTHETIC}$) may be attenuated such that $I_{SYNTHETIC}<I_{K1}$.

In some embodiments, the generating circuit 20 comprises a processor, and the processor is programmed to calculate the value of the inward rectifying current. It will be apparent in light of the present disclosure that the generating circuit 20 may be implemented using a processor (e.g., with software), discrete electronic components, application-specific integrated circuits, field-programmable gate arrays, or combinations of these or other configurations.

The system 10 may comprise a summing circuit 30 configured to add the synthetic inward rectifying current ($I_{SYNTHETIC}$) to the stimulation current ($I_{STIM}$) of the patch clamp 12, producing an input current ($I_{INPUT}$). In this way, the synthetic current is provided to the electrode 14 as a component of the input current.

The system 10 may be used continually such that, in an embodiment having a digital implementation, the membrane voltage is repeatedly measured over time at a sampling frequency, and corresponding synthetic inward rectifying currents are provided to the cell 90 by way of the electrode 14. It should be noted that a plurality of currents may be implemented as a continuous electrical current that varies over time according to the synthetic current for each time period.

The generating circuit 20 may further comprise a switch 24 for selectively disconnecting the generating circuit 20 such that no synthetic inward rectifying current is provided to the electrode 14.

Figure 6:
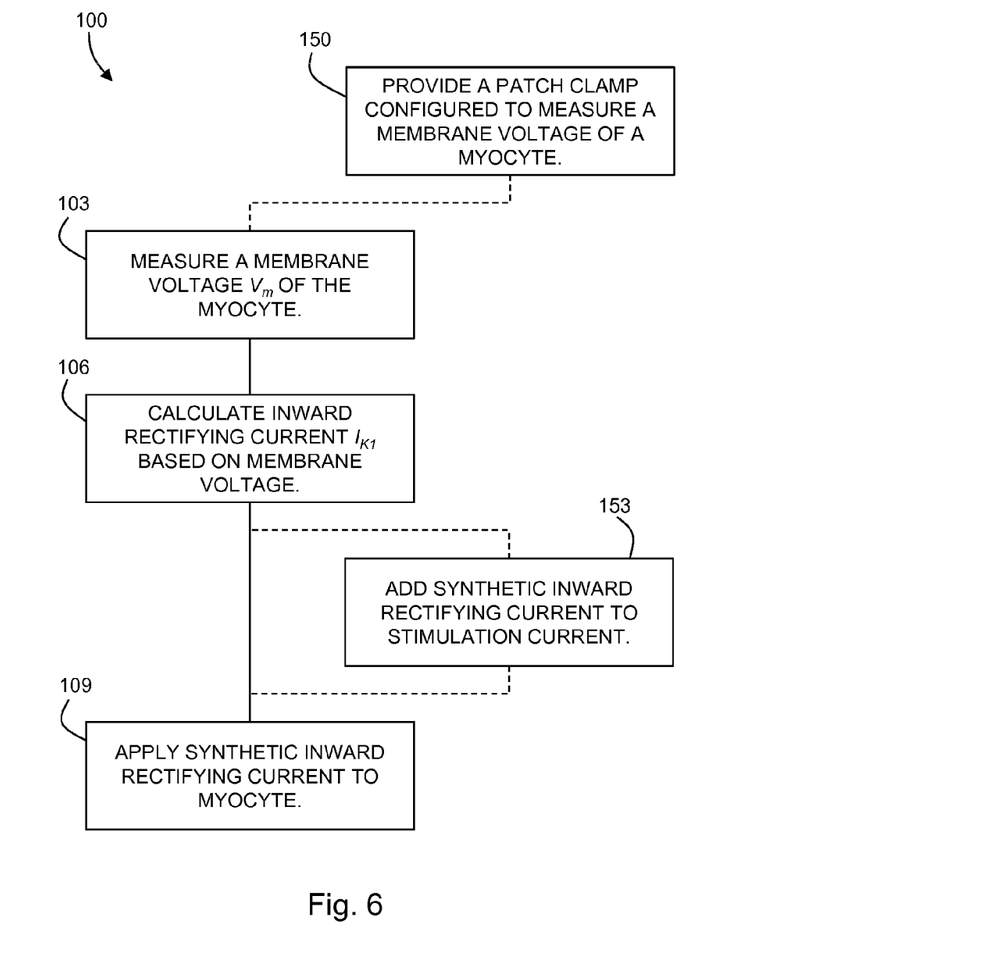
FIG. 6 is a flowchart depicting a method according to an embodiment of the present invention.

The present disclosure may be embodied as a method 100 for producing regular action potentials from an iPSC-derived myocyte (see, e.g., FIG. 6). The method 100 comprises the step of measuring 103 a membrane voltage ($V_m$) of the myocyte. For example, a patch clamp may be used in a whole-cell configuration to measure 103 the membrane voltage. A value of an inward rectifying current ($I_{K1}$) is calculated 106 based on the measured membrane voltage. In some embodiments, the value is calculated 106 according to equation (1), above. In some embodiments, the value is calculated 106 using a processor. For example, a computer may be configured to receive the measured 103 membrane voltage and programmed to calculate 106 an inward rectifying current based on the received membrane voltage. Other techniques for calculating 106 the inward rectifying current will be apparent in light of the present disclosure.

The method 100 further comprises the step of applying 109 a synthetic inward rectifying current ($I_{SYNTHETIC}$) to the myocyte thereby causing the myocyte to produce regular action potentials. The current may be applied 109 by way of an electrode of a patch clamp. The synthetic inward rectifying current corresponds to the calculated 106 value. In some embodiments, the applied 109 synthetic current is equal to the calculated 106 inward rectifying current. In some embodiments, the applied 109 synthetic current is less than the calculated 106 value, for example, where a potentiometer is used to attenuate the current.

In some embodiments, a patch clamp is provided 150 and configured to measure 103 a membrane voltage of the myocyte using an electrode. The patch clamp can be configured as a current clamp, and a stimulation current ($I_{STIM}$) is applied to the myocyte. In such an embodiment, the synthetic inward rectifying current may be added 153 to the stimulation current to produce an input current $I_{INPUT}$ which is applied to the myocyte by way of the electrode. As such, the synthetic current is applied 109 to the myocyte as a component of the input current.

The method may further be used to determine whether an iPSC-derived myocyte exhibits ventricular features or atrial features. For example, a method 200 may include the step of sampling 203 a membrane voltage of an iPSC-derived myocyte over a period of time and at a sampling frequency (see, e.g., FIG. 7). A plurality of values of synthetic inward rectifying currents is calculated 206, each value corresponding to a sampled 203 membrane voltage. The values may be calculated 206 according to equation (1). The method 200 comprises the step of applying 209 a synthetic inward rectifying current to the myocyte according to the calculated 206 values of inward rectifying current. The myocyte may be determined 212 to exhibit ventricular features or atrial features based on the action potentials based on the morphology of the resulting action potentials.

Figure 7:
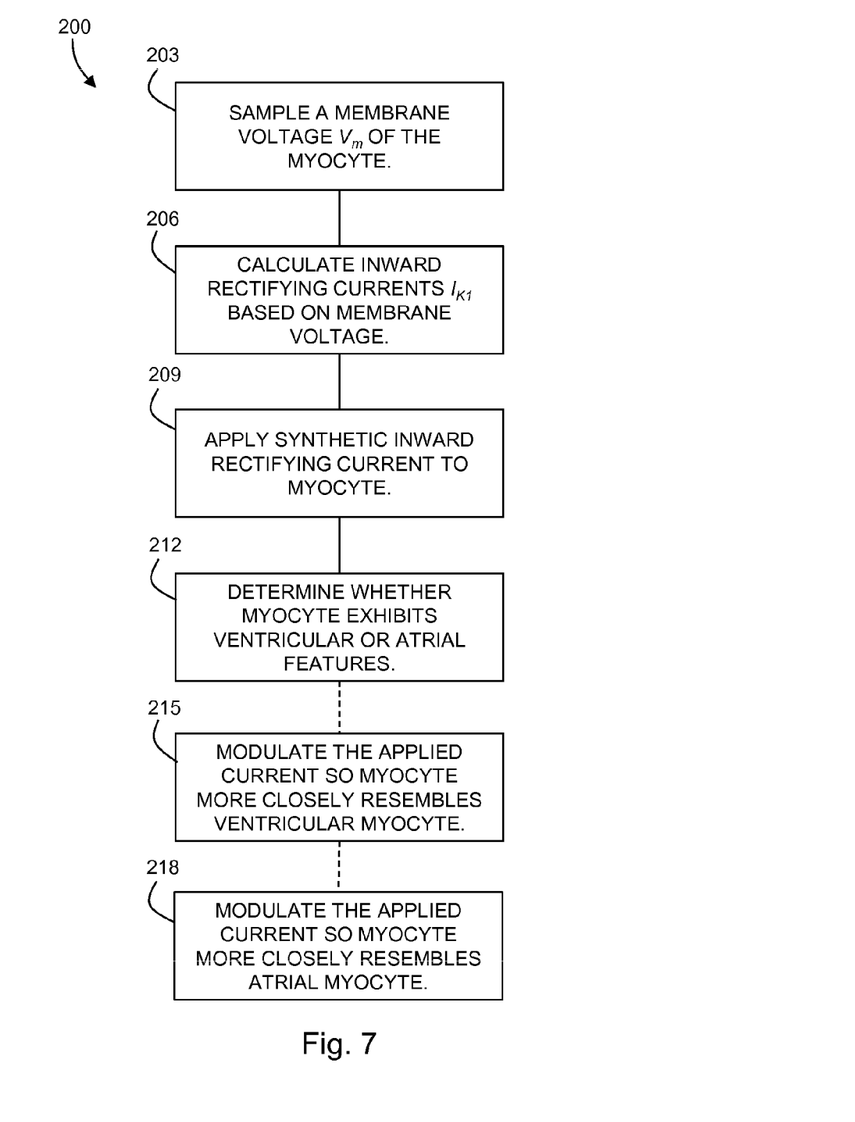
FIG. 7 is a flowchart depicting a method according to another embodiment of the present invention.

If the myocyte is determined 212 to exhibit ventricular features, the method 200 may include the step of modulating 215 the applied 209 synthetic inward rectifying current such that the action potential of the myocyte more closely matches the action potential of a ventricular myocyte. If the myocyte is determined 212 to exhibit ventricular features, the method 200 may include the step of modulating 218 the applied 209 synthetic inward rectifying current such that the action potential of the myocyte more closely matches the action potential of a ventricular myocyte.

Figure 8:
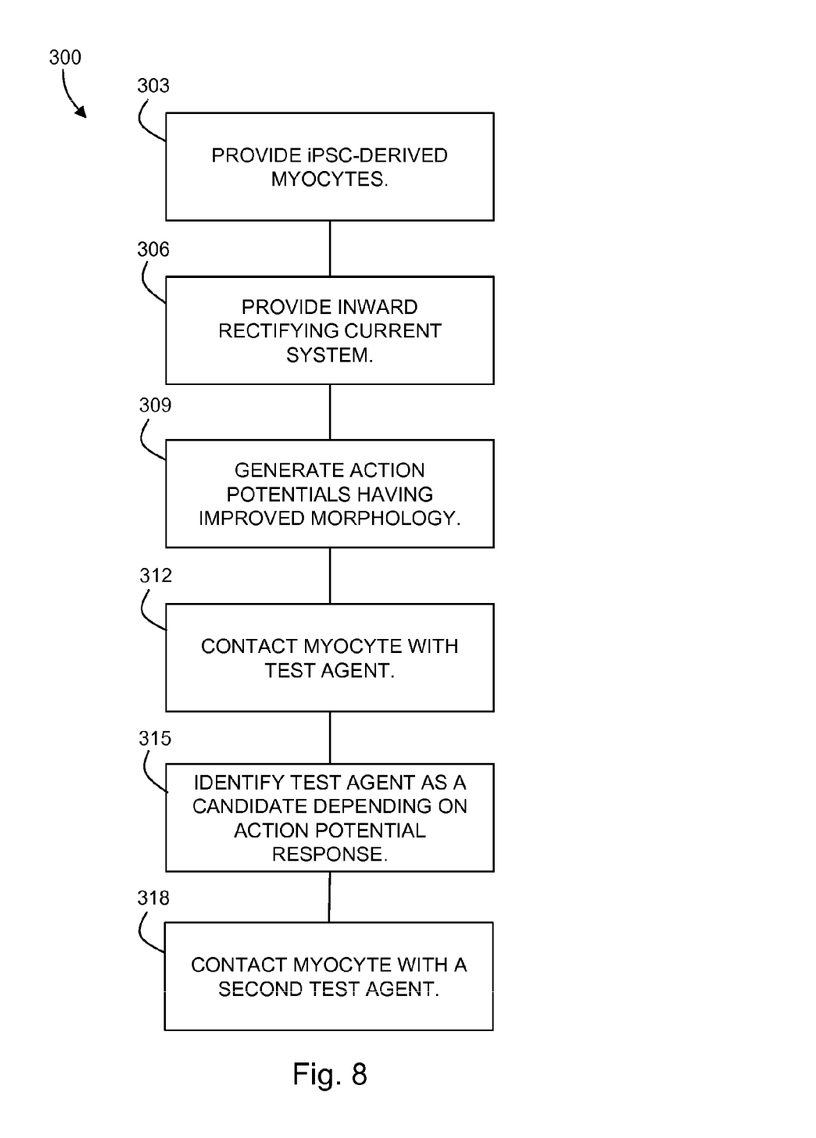
FIG. 8 is a flowchart depicting a method according to another embodiment of the present invention.

The present disclosure may be embodied as a method 300 for identifying test agents for drug development (see, e.g., FIG. 8). The method 300 comprises the steps of providing 303 iPSC-derived cardiac myocytes and providing 306 a system for applying a synthetic inward rectifying current, such as the system 10 described above. A pattern of action potentials having improved morphology is generated 309 using the system. The myocyte may exhibit action potentials characteristic of a ventricular myocyte or an atrial myocyte. The myocyte is contacted 312 with a test agent. The test agent is identified 315 as a candidate for drug development based on characteristics of the action potentials of the myocyte. For example, the test agent may be identified 315 as a candidate if the characteristics of individual action potentials is changed such that action potentials become more or less triangular in shape, become prolonged or shortened, the regularity of the action potentials is changed, there are changes in the refractory period, or there are changes in the restitution behavior. In other examples, without limitation, the action potential is changed in its duration, degree of triangulation, refractory period, restitution steepness, threshold for development of alternans, or threshold for unstable or chaotic behavior. The method 300 may further comprise the step of contacting 318 the iPSC-derived myocyte to a second test agent (after contacting 312 the myocyte with the (first) test agent as described above). The second test agent may be selected to restore the changed characteristics of the myocyte to the characteristics prior to contact 312 with the first test agent.

The described methods have many applications. For example, a method will allow comprehensive analysis of human electrophysiological system. iPSC cardiocytes can be used in the interpretation of channelopathies, drug screening, and the assessment of potential arrhythmogenesis. By eliminating many of the potentially confounding non-physiological consequences of spontaneous activity and unstable behavior of human iPSC-derived cardiac myocytes, this method provides a useful tool for studying the dynamics of repolarization. It has applications for research studies looking at genetic regulation of repolarization in disease states, as well as serving as an aid in the interpretation of data from drug studies and the proarrhythmic potential of safety screens.

The system and methods described in the present disclosure can be used for iPSCs from humans or from other animals, including, for example, mammals.

The following example is provided to further illustrate the invention.

Example

Methods
 Cell Preparation
 Commercially-available iPSC-derived cardiac myocytes (iCell Dynamics, WI), were prepared according to manufacturer's instructions. Briefly, ICELL® cardiac myocytes (cryopreserved single-cell suspensions in 1 ml cryovials) were stored in liquid nitrogen. Vials were thawed in a waterbath (37° C.). Cells were washed then rinsed with 1 ml of RT "ICELL® Cardiomyocyte Plating Medium." An additional 8 ml of plating medium was added and cells mixed with solution by gentile inversion. Cardiocytes were seeded on 15 mm cover-slips coated with 0.01% (w/v) gelatin solution in 12-well plates. Cardiocytes were seeded (20,000-40,000/dish) in 2 ml of RT plating medium, permitting single cell culture, and incubated for 2+ days at 37° C., 7% $CO_2$. Non adherent cells were removed by rinsing with "ICELL® Cardiomyocyte Maintenance Medium." A further 2 ml of maintenance medium was added. Maintenance medium was changed every 2 days, and cells were used within 1 week.

Electrophysiology
 iPSC-derived cardiocytes were voltage clamped. Currents were recorded using whole-cell clamp at RT. Cells in the recording chamber (300 µl) were continuously perfused with Tyrode. Pipettes fabricated from borosilicate glass (Flaming/Brown horizontal micropipette puller) and tips heat-polished (NARISHIGE® microforge). Pipettes contained (mM): 10 NaCl, 125 KCl, 1 $MgSO_4$, 5 EGTA, 5 ATP (Mg salt), 5 Tris-creatinephosphate, 0.3 GTP, 10 HEPES, pH 7.2. Extracellular solution (mM): 150 NaCl, 5.4 KCl, 0.5 $Na_2HPO_4$, 1 $MgCl_2$, 2 $CaCl_2$), 10 glucose, 10 HEPES, pH7.4. After establishing a seal (1-10 Gohm), suction and voltage pulses were used to rupture the patch. Currents were recorded (Axopatch-1D, Molecular Dynamics, CA) and interfaced to a PENTIUM® 4 computer via a DIGIDATA® 1322A (Molecular Dynamics, CA). PCLAMP® 9.0 (Molecular Dynamics, CA) was used to control protocols and data acquisition.

In Silico Interface
 We used an Analog and Digital I/O board PCIe-DAS1602/16 (Measurement Computing Corporation) installed on a on a DELL PRECISION® T7500 workstation with 2 INTEL® XEON® CPU E5520 to transfer the $V_m$ signal to the signal of $I_{K1}$ current. Source code is in the supplement.

Data Analysis.
 Analysis was performed using PCLAMP® 9 (Molecular Dynamics). Action potential duration (APD) was computed for 50% ($APD_{50}$) and 90% ($APD_{90}$) of repolarization in ms. Maximum rate of rise of the AP upstroke was determined ($dV_m/dt_{max}$) in mV/ms. Resting membrane potential was recorded prior to each AP. For spontaneous APs, the diastolic characteristics were reported for the period of time between complete AP repolarization and the beginning of depolarization in the subsequent AP. Duration, and minimum/mean potentials were computed for the diastolic period.

Statistical Analysis
 Results are reported as mean±s.e.m. Differences were analyzed by t-test or ANOVA as appropriate and $p<0.05$ considered statistically significant.

Results
 In order to overcome the lack of $I_{K1}$ in h-iPSC-derived cardiac myocytes, we developed a variation of the dynamic clamp approach to inject a synthetic version of $I_{K1}$ (FIG. 1). The center of the system is the isolated h-iPSC-derived cardiac myocyte under whole cell voltage or current clamp. Whole cell clamp is accomplished with a gigaseal under conventional current clamp mode. The membrane voltage of the cardiac myocyte is output from the amplifier and fed into a computer via a digitizer which calculates the inward rectifier current for the membrane potential, according to the equation shown in FIG. 1. The calculated value of $I_{K1,Synthetic}$ is passed through a potentiometer (used to adjust amplitude without sacrificing digital resolution) to scale $I_{K1}$ and then summed with the standard stimulation input from PCLAMP®. A switch allows rapid changes between conventional current clamp and summed input. When the summed input is switched on, the myocyte receives the sum of two inputs: the standard AP stimulus current plus $I_{K1,Synthetic}$ from the real-time current simulator. The standard voltage clamp electronics can be driven via the summing circuit without modification of conventional voltage clamp and data recording with only minor software selection changes of input/output channels. The result is a cell that behaves as though it were expressing a native $I_{K1}$ that had instantaneously been "transfected" into the cell.

Properties and Variability of iPSC-Derived Cardiac Myocyte APs.

Figure 2:
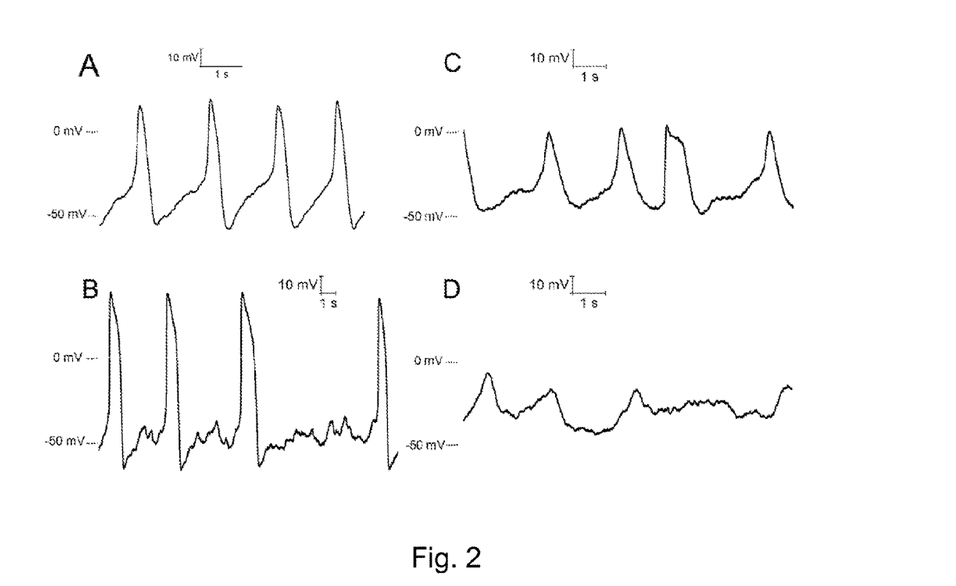
FIG. 2: Spontaneous APs from iPSC-derived cardiac myocytes. (A) Typical spontaneous APs, with relatively slow diastolic depolarization typical of pacemaker type cells and a very slow upstroke ($dV/dt_{max}$). (B) Example of irregular and DAD-like behavior. Generally, spontaneous activity during current clamp showed substantial irregularity. This irregularity often had a diastolic interval which was largely flat with noisy behavior and sudden spontaneous increases in potential preceding initiation of the action potential. (C,D): Examples of EAD-like behavior in the same cells. In c, there is a high voltage prolongation of the AP in a single beat around 0 mV. In d, the cell spent a prolonged time in a low voltage (−20 to −40 mV) EAD-like oscillation.

The majority of reports from iPSC-derived cardiocytes indicate they are generally spontaneously active, with a few quiescent cells, which is consistent with our findings. Consequently, most AP studies to date on iPSC-derived cardiocytes have reported parameters based on analysis of spontaneous AP behavior. Given the high degree of cell to cell variability, large numbers of cells have been used to produce statistically significant results in changes in AP parameters. High throughput screening methods have even been employed to examine cellular properties of commercially-available iPSC-derived cardiac myocytes. This reflects at least in part, variability between cell types, i.e., ventricular, atrial, and nodal cells. However, some of this variability also results from the consequences of recording from spontaneously active cells. The average maximum diastolic potential for spontaneously active cells was −59±2 mV (n=33). Spontaneous activity was usually irregular and occurred over a broad range of diastolic intervals from a few hundred ms to 8 s (average: 2068±415 ms, n=25) and included a high beat to beat variability for any given single cell (see FIG. 2). Not surprisingly, variability in heart rate was accompanied by high variability in AP duration and shape. As shown in Table 1, the spontaneous APs tended to have a relatively short amplitude and a very slow upstroke (FIG. 2A,B). This irregular behavior was often accompanied by spontaneous events resembling EADs and low and high threshold DADs (FIG. 2C,D).

TABLE 1

AP parameters and beat to beat variations expressed as mean ± s.e.

|  | Resting Potential (mV) | AP Amplitude (mV) | $dV/dt_{max}$ (mV/ms) |
|---|---|---|---|
| Spontaneously beating cells (n = 25) | −63 ± 5.8 | 83 ± 11 | 15 ± 6 |
| Stimulated cells (n = 21) | −63 ± 3.5 | 90 ± 6 | 85 ± 6 |
| Stimulated cells with artificial $I_{K1}$ (n = 31) | −84 ± 0.1 | 132 ± 2 | 147 ± 11 |

Figure 3:
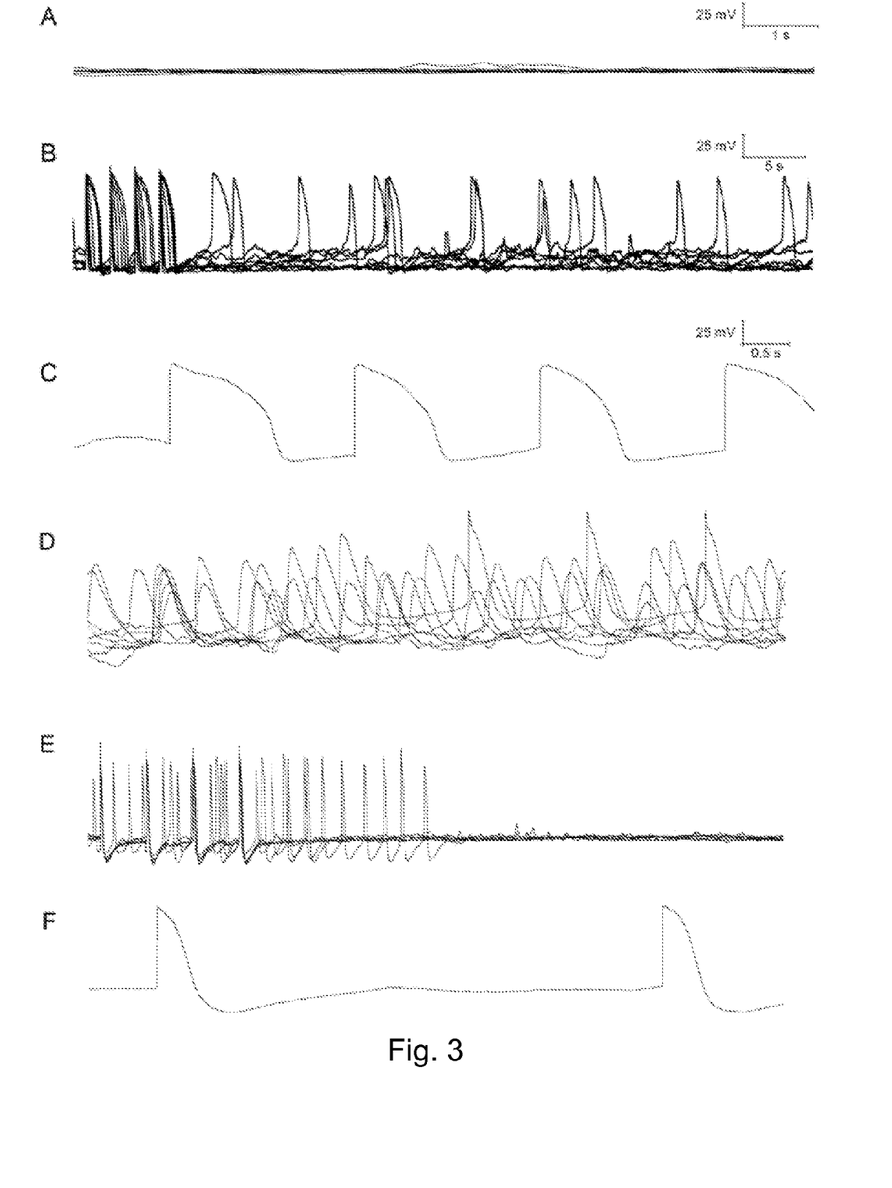
FIG. 3. Pacing quiescent and spontaneously active cells. (A) Typical resting potential of a quiescent cell without any stimulation. (B) Stimulating (0.5 Hz for 4 beats) a quiescent cell (same as in (A)) initiates complex behavior and automaticity. (C) Expanded time scale showing stimulated APs. (D) Spontaneous activity, highly variable in frequency, diastolic potential, overshoot and shape. (E) Pacing (0.25 Hz for 4 beats) a spontaneously active cell (myocyte as in (D)), produces a more consistent after-hyperpolarization potential and changes spontaneous activity. (F) The after-hyperpolarization can be seen more readily on an expanded time scale.

One strategy to reduce variability in electrical activity is through paced external stimulation. This can regularize slow spontaneous activity and potentially induce regenerative electrical behavior in quiescent cells. Not all iPSC-derived cardiac myocytes were spontaneously active (out of 33 cells tested, 8 were not spontaneously active). However, even cells which are not spontaneously active do not exhibit normal AP characteristics associated with human adult myocardial cells from the working myocardium. The lack of spontaneous contractile function can be due to a stable normal resting potential (around −85 mV) or may due to a relatively depolarized potential, which results in an abnormal resting state. The majority of the non-spontaneous cells did not have a hyperpolarized resting membrane potential typical of working myocardium, but were in an abnormally depolarized state. Three out of 8 non-spontaneously active cells had a resting potential above −60 mV and only 1 had a resting membrane potential below −70 mV. APs and contractile activity could be initiated in quiescent cells by pacing with a stimulus current. The elicited APs resembled those from spontaneously active cells. In some quiescent cells, pacing could elicit a following period of spontaneous behavior (FIG. 3A-C), indicating that delayed rectifier currents produce the diastolic potential in human iPSC-derived cardiac myocytes. Pacing of spontaneously active tissue altered beat to beat variability (FIG. 3 D-F) and improved some other parameters, particularly $dV/dt_{max}$ (Table 1).

Figure 4:
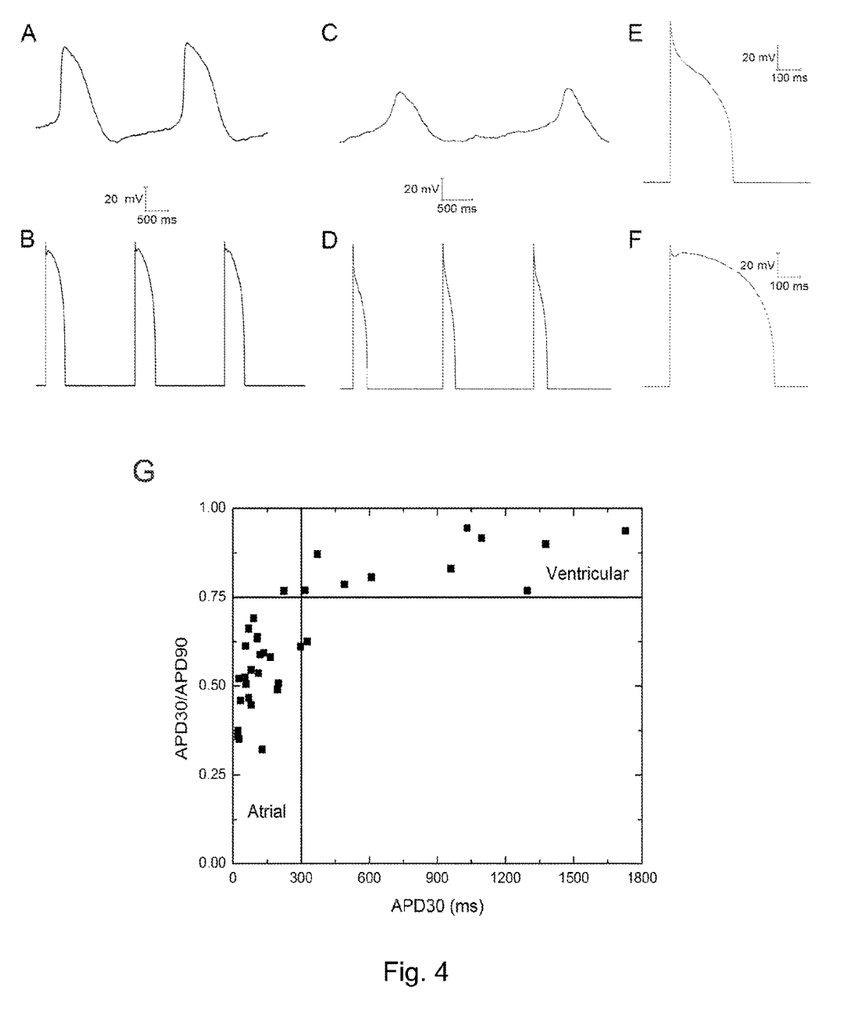

Regardless of whether APs arose from spontaneous activity or stimulated pacing, they had prolonged repolarization ($APD_{90}$ was 955±103 ms (n=38) and 967±141 ms (n=30) respectively), diminished amplitude and a reduced maximum upstroke ($dV/dt_{max}$) compared with APs from freshly isolated human atrial or ventricular cardiocytes. They also lacked the spike and dome morphology typical of ventricular and atrial myocytes. This was somewhat surprising since the cells uniformly express robust $I_{to}$ that gives rise to this AP morphology. However, the Kv4.2/4.3 mediated channels that give rise to this current have substantial closed state inactivation and may be largely inactivated by the depolarized state of the spontaneous and stimulated APs. Similarly, $I_{Na}$ will also be inactivated at these potentials and cannot contribute fully to the normal rapid upstroke or the spike and dome behavior. The lack of these behaviors will lead to non-physiological function and greatly diminish the predictive value of any screens for pro-arrhythmic or anti-arrhythmic behavior of mutant channels or candidate drugs. However, when we injected $I_{K1,Synthetic}$, a stable resting membrane potential was established and there was a marked change in AP shape and regularity (FIG. 4). Spike and dome morphology is clearly seen, and the difference between ventricular-like and atrial-like myocytes is readily apparent, suggesting that this method allows efficient discrimination between cell types. FIG. 4G shows that cells fall into two distinct populations, based on action potential shape and duration. The variance between APs both from beat to beat and from cell to cell was reduced and the rapid upstroke ($dV/dt_{max}$) of the rising phase of the AP was prominent and consistent (Table 1). Clearly, reconstitution of $I_{K1}$ restores many important properties to the h-iPSC-derived cardiac myocytes.

Pharmacological Manipulation of Repolarization

Figure 5:
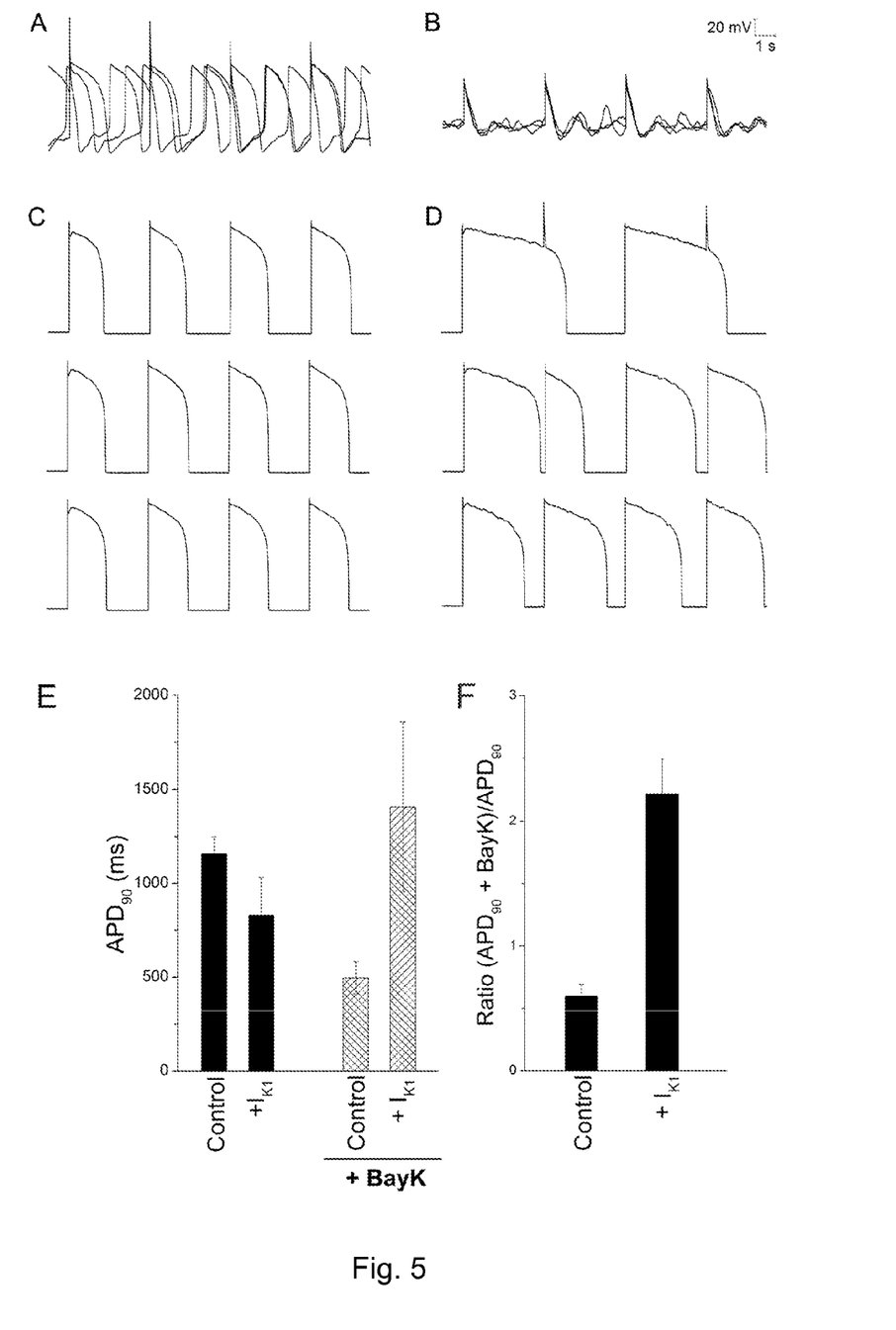

Reconstitution of the inward rectifier normalizes many of the properties of h-iPSC-derived cardiocyte APs into a form more clearly resembling working cardiac myocytes. Furthermore, it relieves many of the uncontrolled properties associated with free-running or stimulated APs. The functional utility of this property can be seen by assessing the calcium channel agonist BayK-8644, which increases the amplitude and disrupts inactivation of the L-type calcium channel, resulting in a profound increase in APD. We examined the effect of 1 μM BayK-8644 on paced h-iPSC-derived cardiac myocytes with and without electronic $I_{K1}$ (FIG. 5). Application of 1 μM BayK-8644 had profound effects in both cases. However, AP prolongation by BayK-8644 was not uniformly observed in paced cells. Rather, a termination of spontaneous full scale AP activity occurred due to membrane depolarization after stimulation of a very foreshortened AP. Increased low level fibrillatory-like electrical oscillations were also observed. In contrast, when $I_{K1}$ was electronically inserted, cellular activity was regularized, variability was reduced and the AP was more physiologica, and the fibrillatory-like electrical behavior was suppressed. Application of BayK-8644 then resulted in clear AP prolongation. At shorted pacing intervals, some APs were prolonged beyond the pacing rate (FIG. 5D). When viewed using paired data, this qualitative difference in predicted arrhythmogenic potential is clearly evident (FIG. 5E) and emphasizes the ability of electronic $I_{K1}$ expression to improve the predictive ability of the human iPSC-derived cardiac myocyte system as a tool for drug safety and the study of the molecular basis of arrhythmias.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

We claim:

1. A method for identifying test agents for drug development comprising:
   a) providing induced pluripotent stem cell (iPSC)-derived cardiac myocytes;
   b) providing a system for producing action potentials by an iPSC-derived cardiac myocyte comprising:
      a patch clamp comprising an electrode configured to measure a membrane voltage ($V_m$) of the myocyte;
      a generating circuit in electronic communication with the electrode, the generating circuit comprising a processor programmed to:
         calculate a value of a synthetic inward rectifying current based on a membrane voltage ($I_{K1}$) based on the membrane voltage; and
         provide to the electrode, a synthetic inward rectifying current according to the determined value to produce action potentials having improved morphology from the myocyte,
      and wherein the generating circuit is configured to:
         calculate a value of an inward rectifying current ($I_{K1}$) based on the membrane voltage;
         provide to the electrode, a synthetic inward rectifying current according to the determined inward rectifying current, to produce the action potentials from the myocyte; and
         repeatedly calculate a value and provide a current at a sampling frequency;
   c) generating a pattern of action potentials in the iPSC-derived myocyte using the system in b);
   d) contacting the iPSC-derived cardiac myocyte with a test agent; and
   e) identifying the test agent as a candidate for drug development if the characteristics of the individual action potential or the regularity of action potentials are changed.

2. The method of claim 1, wherein the iPSC-derived cardiac myocyte exhibits action potentials characteristic of the action potential of an atrial myocyte.

3. The method of claim 1, wherein the iPSC-derived cardiac myocyte exhibits action potentials characteristic of the action potential of a ventricular myocyte.

4. The method of claim 1, wherein the individual action potential is changed in its duration, degree of triangulation, refractory period, restitution steepness, threshold for development of alternans, or threshold for unstable or chaotic behavior.

5. The method of claim 1, wherein the test agent in step d) is a first test agent and further comprising the step of contacting the iPSC-derived myocyte from step e) to a second test agent that can restore the changed characteristics to the characteristics prior to contact with the first test agent.

6. The method of claim 1, wherein the provided iPSC-derived cardiac myocytes are human.

7. The method of claim 1, wherein the value of the synthetic inward rectifying current is determined according to the equation:

$$I_{K1} = 0.5\left(\frac{V_m + 85}{1 + e^{0.0896(V_m+85)}}\right) + 0.01(V_m + 85).$$

* * * * *